(12) United States Patent
Chiao

(10) Patent No.: US 8,536,188 B2
(45) Date of Patent: Sep. 17, 2013

(54) DOSING REGIMENS FOR TREATMENT OF PROLIFERATIVE DISORDERS COMPRISING ADMINISTRATION OF SAPACITABINE

(75) Inventor: Judy H. Chiao, Berkeley Heights, NJ (US)

(73) Assignee: Cyclacel Limited, London (GB)

( * ) Notice: Subject to any disclaimer, the term of this patent is extended or adjusted under 35 U.S.C. 154(b) by 386 days.

(21) Appl. No.: 12/597,293

(22) PCT Filed: Apr. 24, 2008

(86) PCT No.: PCT/GB2008/001424
§ 371 (c)(1),
(2), (4) Date: Oct. 23, 2009

(87) PCT Pub. No.: WO2008/132443
PCT Pub. Date: Nov. 6, 2008

(65) Prior Publication Data
US 2010/0125084 A1    May 20, 2010

(30) Foreign Application Priority Data
Apr. 25, 2007  (GB) .................................. 0708021.1
Dec. 4, 2007   (GB) .................................. 0723723.3

(51) Int. Cl.
*A61P 35/00* (2006.01)

(52) U.S. Cl.
USPC ........................................................ 514/274

(58) Field of Classification Search
None
See application file for complete search history.

(56) References Cited

U.S. PATENT DOCUMENTS

2005/0014716 A1 * 1/2005 Wang et al. ..................... 514/50

FOREIGN PATENT DOCUMENTS

WO    2007/132228 A1    11/2007
WO    2008/075042 A1    6/2008

OTHER PUBLICATIONS

Delaunoit et al. (Investigational New Drugs, 24:327-333, 2006).*
Gilbert et al. (Invest new Drugs 24:499-508, 2006).*
Hanaoka et al. (Int J. Cancer, 82:226-236, 1999).*
Burch, P.A. et al., "Phase I Study of Orally Administered CS-682 in Solid Tumors," Proceedings of ASCO, vol. 20:92a, Poster Presentation No. 364 (2001).
Sankyo Co., Ltd., "CS-682, Antineoplastic Antimetabolite," Drugs of the Future, vol. 24(9):957-960 (1999).
Tolcher, A. et al., "Phase I study of sapacitabine, an oral nucleoside analogue, in patients with refractory solid tumors or lymphomas," European Journal of Cancer, Supplement, vol. 4(12):142, Poster Presentation No. 463 (2006).
Galmarini, Carlos M. et al., "Drug evaluation: Sapacitabine—an orally available antimetabolite in the treatment of cancer," Current Opinion in Investigational Drugs, vol. 7(6):565-573 (2006).

* cited by examiner

*Primary Examiner* — Bong-Sook Baek
(74) *Attorney, Agent, or Firm* — Nelson Mullins Riley & Scarborough LLP; Cynthia L. Kanik

(57) ABSTRACT

One aspect of the present invention relates to the use of sapacitabine, or a metabolite thereof, in the preparation of a medicament for treating a proliferative disorder, wherein the sapacitabine or metabolite thereof is administered in a dosing regimen comprising at least one treatment cycle, wherein said treatment cycle comprises administering a therapeutically effective amount of sapacitabine or metabolite thereof for about 2 to about 6 days per week, for 2 weeks out of 3 weeks. Another aspect of the invention relates to the use of sapacitabine, or a metabolite thereof, in the preparation of a medicament for treating cutaneous T-cell lymphoma (CTCL).

17 Claims, No Drawings

DOSING REGIMENS FOR TREATMENT OF PROLIFERATIVE DISORDERS COMPRISING ADMINISTRATION OF SAPACITABINE

RELATED APPLICATIONS

The present application is a 35 U.S.C. 371 national stage filing of International Application No. PCT/GB2008/001424, filed Apr. 24, 2008, which claims priority to Great Britain Application Nos. 0708021.1, filed Apr. 25, 2007 and 0723723.3, filed Dec. 4, 2007. The entire contents of each of these applications are hereby incorporated by reference herein.

The present invention relates to therapeutic uses and dosing regimens for the compound 1-(2-C-cyano-2-deoxy-β-D-arabino-pentofuranosyl)-N4-palmitoylcytosine or a metabolite thereof, otherwise known as sapacitabine.

BACKGROUND TO THE INVENTION

Nucleoside analogues represent a major group of antitumour cytotoxic drugs. For example, the therapeutic use of pyrimidine nucleosides in the treatment of proliferative disorders has been well documented in the art. Commercially available antitumour agents of the pyrimidine series include 5-fluorouracil (Duschinsky, R., et al., J. Am. Chem. Soc., 79, 4559 (1957)), Tegafur (Hiller, S A., et al., Dokl. Akad. Nauk USSR, 176, 332 (1967)), UFT (Fujii, S., et al., Gann, 69, 763 (1978)), Carmofur (Hoshi, A., et al., Gann, 67, 725 (1976)), Doxyfluridine (Cook, A. F., et al., J. Med. Chem., 22, 1330 (1979)), Cytarabine (Evance, J. S., et al., Proc. Soc. Exp. Bio. Med., 106. 350 (1961)), Ancytabine (Hoshi, A., et al., Gann, 63, 353, (1972)) and Enocytabine (Aoshima, M., et al., Cancer Res., 36, 2726 (1976)). Cytarabine (ara-C) and fludarabine are the two most active drugs against leukemias, whereas, gemcitabine and 5-fluorouracil are active against a wide range of solid tumours.

The nucleoside analogues currently available for use in clinic are prodrugs which are not active by themselves. Upon entering cells, these nucleoside analogues are phosphorylated by nucleoside kinases and the phosphorylated metabolites are incorporated into DNA causing a pause in, or termination of, DNA synthesis. The close correlation between the degree of drug-induced cell death and the amount of incorporated analogue molecules in cellular DNA strongly suggests that the incorporation of these molecules into DNA is a key cytotoxic event (Azuma A et al; 2'-C-cyano-2-deoxy-β-D-arabino-pentafuranosyl cytosine: a novel anticancer nucleoside analog that causes both DNA strand breaks and G2 arrest; Molecular Pharmacology, 59 (4), 725-731, 2001).

The clinical effectiveness of nucleoside analogues appears to be influenced by multiple factors including the substrate specificities of nucleoside kinases, the expression levels of kinases in tumour tissues, and the rate of metabolic elimination by inactivating enzymes (Azuma A et al; ibid; Matsuda A and Sasak T, Antitumour activity of sugar-modified cytosine nucleosides; Cancer Science. 95 (2), 105-111, 2004). Rationally designed nucleoside analogues with improved biochemical properties may be more effective antitumour agents.

2'-C-Cyano-2'-deoxy-β-D-arabino-pentafuranosylcytosine (CNDAC) is a rationally designed analogue of deoxycytidine. It causes single-strand DNA breakage that cannot be repaired by ligation. This type of DNA damage is different from that caused by other nucleoside analogues such as ara-C and gemcitabine, which terminate or pause DNA synthesis at the site of incorporation [Azuma A et al; ibid]. This unique strand-breaking action seems to be the basis of CNDAC's ability to induce cell cycle arrest at the G2 phase, as distinct from the S-phase block seen with ara-C or gemcitabine. During the drug discovery phase, many derivatives of CNDAC were synthesized and investigated for stronger antitumour activity than CNDAC. For example, EP 536936 (Sankyo Company Limited) discloses various T-cyano-2'-deoxy-derivatives of 1-β-D-arabinofuranosylcytosine which have been shown to exhibit valuable anti-tumour activity. One particular compound disclosed in EP 536936 is 2'-cyano-2'-deoxy-N$^4$-palmitoyl-1-β-D-arabinofuranosylcytosine (referred to hereinafter as "sapacitabine" or "CYC682" or "CS-682"); sapacitabine has been chosen for clinical development because of its broad range of antitumour activity in preclinical studies.

Sapacitabine, also known as 1-(2-C-cyano-2-deoxy-β-D-arabino-pentofuranosyl)-N$^4$-palmitoyl cytosine, (Hanaoka, K., et al, Int. J. Cancer, 1999: 82:226-236; Donehower R, et al, Proc Am Soc Clin Oncol, 2000: abstract 764; Burch, P A, et al, Proc Am Soc Clin Oncol, 2001: abstract 364), is an orally administered novel 2'-deoxycytidine antimetabolite prodrug of CNDAC.

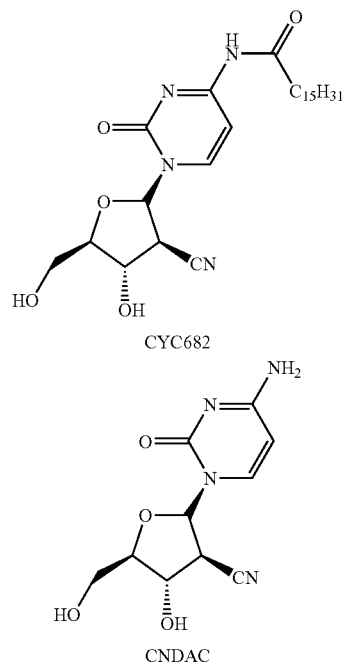

Sapacitabine has been the focus of a number of studies in view of its oral bioavailability and its improved activity over gemcitabine (the leading marketed nucleoside analogue) and 5-FU (a widely-used antimetabolite drug) based on preclinical data in solid tumours. Recently, investigators reported that sapacitabine exhibited strong anticancer activity in a model of colon cancer. In the same model, sapacitabine was found to be superior to either gemcitabine or 5-FU in terms of increasing survival and also preventing the spread of colon cancer metastases to the liver (Wu M, et al, Cancer Research, 2003: 63:2477-2482). To date, phase I data from patients with a variety of cancers suggest that sapacitabine is well tolerated in humans, with myelosuppression as the dose limiting toxicity.

Following oral administration, sapacitabine is converted to CNDAC by amidases and esterases in the gut, plasma, and liver. CNDAC can be converted to CNDAC-mono phosphate by deoxycytidine kinase which is thought to be the rate-limiting step in the formation of CNDAC-triphosphate (CNDACTP). CNDACTP is the active metabolite of sapacitabine and exerts its cytotoxic effects via the following mechanisms: a) potent inhibition of DNA polymerase, b) cessation of DNA strand elongation by incorporation into DNA strands, and c) breakage of DNA strands at the 3'-diester bond of CNDAC after its incorporation into the DNA. This latter mechanism is considered to be a novel effect that is not exhibited by other nucleoside analogues. CNDAC-phosphates can be degraded by cytidine deaminase and 5'-nucleotidase. However, compared with ara-C, CNDAC is a weak substrate of cytidine deaminase.

In addition to the antitumour activity of its metabolite, the parent drug sapacitabine itself is cytotoxic against a variety of cancer cell lines, including those lacking deoxycytidine kinase. This suggests that the antitumour activity of sapacitabine in vivo is likely to be mediated by both the parent drug as well as its active metabolite, CNDAC. The cellular pharmacology of sapacitabine is currently under investigation.

Sapacitabine and its active metabolite, CNDAC, showed a broad spectrum of activity against human tumour cells from various organs. In human tumour xenograft models, sapacitabine was active against a variety of tumours, and was especially effective against gastric, mammary, lung, colorectal, and hepatic tumour xenografts where tumour regressions were observed. Although sapacitabine showed a partial cross-resistance to ara-C-resistant tumour cell lines, it was active in vivo against P388 leukemia cell lines resistant to mitomycin C, vincristine, 5-FU, or cisplatin. In a mouse P388 leukemia model and in human xenografts of poorly differentiated gastric adenocarcinoma, sapacitabine exhibited much more potent antitumour activity than 5'-DFUR and gemcitabine.

Single-dose toxicity studies in rodents, and repeat dose studies of up to 3 months duration in mice and dogs have been completed. Sapacitabine has a direct toxic effect on rapidly proliferating cells, which is consistent with the known side effects of cytotoxic drugs. The major toxicities are hematopoietic, gastrointestinal, and testicular. The toxicities appear to be similar between single and repeat dosing, as well as between species.

In summary, sapacitabine, a rationally designed nucleoside analogue, may be a more efficacious antitumour agent than other nucleoside analogues. Its oral route of administration is more convenient for patients as compared with the intravenous administration route required by other nucleoside analogues.

The present invention seeks to provide new therapeutic applications for sapacitabine, and further seeks to provide improved dosing regimens for sapacitabine in the treatment of new and existing therapeutic applications.

STATEMENT OF INVENTION

A first aspect of the invention relates to the use of sapacitabine, or a metabolite thereof, in the preparation of a medicament for treating a proliferative disorder, wherein the sapacitabine or metabolite thereof is administered in a dosing regimen comprising at least one treatment cycle, wherein said treatment cycle comprises administering a therapeutically effective amount of sapacitabine or metabolite thereof for about 2 to about 6 days per week, for 2 weeks out of 3 weeks.

Prior art sapacitabine dosing regimens typically involve administering the active agent over extended durations, for example, for 7 or 14 consecutive days in a 21 day cycle. Advantageously, the presently claimed dosing regimens maximise drug efficiency, whilst minimising the adverse side effects associated with the treatment. Administering sapacitabine to a patient over a shorter duration followed by a rest period allows higher dosages of sapacitabine to be administered to the patient and has been shown to alleviate certain adverse side effects.

A second aspect of the invention relates to a method of treating a proliferative disorder, said method comprising administering a therapeutically effective amount of sapacitabine, or a metabolite thereof, to a subject in accordance with a dosing regimen comprising at least one treatment cycle, wherein said treatment cycle comprises administering a therapeutically effective amount of sapacitabine or metabolite thereof for about 2 to about 6 days per week, for 2 weeks out of 3 weeks.

A third aspect of the invention relates to the use of sapacitabine, or a metabolite thereof, in the preparation of a medicament for treating cutaneous T-cell lymphoma (CTCL).

A fourth aspect of the invention relates to a method of treating a subject suffering from cutaneous T-cell lymphoma (CTCL), said method comprising administering a therapeutically effective amount of sapacitabine, or a metabolite thereof, to said subject.

A fifth aspect of the invention relates to a pharmaceutical composition for use in the treatment of cutaneous T-cell lymphoma (CTCL) comprising sapacitabine, or a metabolite thereof, and a pharmaceutically acceptable carrier.

A sixth aspect of the invention relates to the use of sapacitabine, or a metabolite thereof, in the preparation of a medicament for treating AML in elderly subjects, wherein the sapacitabine or metabolite thereof is administered in a dosing regimen comprising at least one treatment cycle, wherein said treatment cycle comprises:
(i) administering a therapeutically effective amount of sapacitabine or metabolite thereof for about 2 to about 6 days per week, for 2 weeks;
(ii) a rest period of from about 5 to about 15 days during which no sapacitabine or metabolite thereof is administered.

DETAILED DESCRIPTION

As mentioned above, the present invention relates to the use of sapacitabine, or a metabolite thereof, or a pharmaceutically acceptable salt thereof, in the preparation of a medicament for treating various proliferative disorders, and in particular to improved dosing regimens.

One aspect of the invention relates to the use of sapacitabine, or a metabolite thereof, in the preparation of a medicament for treating a proliferative disorder, wherein the sapacitabine or metabolite thereof is administered in a dosing regimen comprising at least one treatment cycle, wherein said treatment cycle comprises administering a therapeutically effective amount of sapacitabine or a metabolite thereof for about 2 to about 6 days per week, for 2 weeks out of 3 weeks.

Advantageously, the presently claimed dosing regimens maximise drug efficiency, whilst minimising the adverse side effects associated with the treatment, such as immunosuppression, for example. In particular, the present study suggests that administering sapacitabine to a patient over a relatively short duration, followed by a rest period, helps alleviate adverse side effects and allows higher dosages of sapacitabine to be administered.

In one preferred embodiment, the treatment cycle comprises:
(i) administering a therapeutically effective amount of sapacitabine or metabolite thereof for about 2 to about 6 days per week, for 2 weeks; followed by (ii) a rest period of 1 week during which no sapacitabine or metabolite thereof is administered.

In one preferred embodiment, the treatment cycle comprises administering a therapeutically effective amount of sapacitabine for 2 to 6 consecutive days per week, for 2 weeks.

In one preferred embodiment, the treatment cycle comprises administering a therapeutically effective amount of sapacitabine for 2 to 5 consecutive days per week, for 2 weeks.

In one highly preferred embodiment, the treatment cycle comprises administering a therapeutically effective amount of sapacitabine for 5 consecutive days per week, for 2 weeks.

In another highly preferred embodiment, the treatment cycle comprises administering a therapeutically effective amount of sapacitabine for 4 consecutive days per week, for 2 weeks.

In yet another highly preferred embodiment, the treatment cycle comprises administering a therapeutically effective amount of sapacitabine for 3 consecutive days per week, for 2 weeks.

Advantageously, using a dosing period as short as 3 days enables higher dosages of sapacitabine to be administered to the patient, whilst at the same time alleviating adverse side effects associated with the treatment.

In one preferred embodiment, the sapacitabine, or metabolite thereof, is administered twice daily.

In a more preferred embodiment, the sapacitabine, or metabolite thereof, is administered twice daily approximately every 12 hours.

In an even more preferred embodiment, the sapacitabine, or metabolite thereof, is administered twice daily in approximately equal dosages.

In one preferred embodiment, the dosing regimen comprises at least two treatment cycles.

In one preferred embodiment, the cycles are repeated one after another consecutively, with no time lag between cycles, i.e. day 1 of the next cycle begins immediately after day 21 of the preceding cycle.

In another preferred embodiment, the cycles are repeated sequentially with a time lag between sequential cycles, i.e. there is a time delay between day 21 of the preceding cycle and day 1 of the next cycle. Preferably, the time delay is sufficient so as to resolve any treatment-related toxicities. In one preferred embodiment, the cycles are separated by a time period of from 1 to 21 days, more preferably, from 1 to 14 days, even more preferably, from 1 to 7 days.

Preferably, the dosing regimen comprises from two to an infinite number of treatment cycles as dictated by patient tolerability and responsiveness to treatment.

More preferably, the dosing regimen comprises at least three treatment cycles.

In one preferred embodiment, the dosing regimen comprises from two to fifty treatment cycles, more preferably from two to thirty, more preferably still, from two to twenty cycles, even more preferably from two to fifteen cycles.

In one highly preferred embodiment, the dosing regimen comprises from two to ten treatment cycles.

More preferably still, the dosing regimen comprises from two to six treatment cycles.

In one preferred embodiment, the total daily dosage administered is from about 25 to about 600 mg of sapacitabine, more preferably from about 25 to about 225 mg, more preferably still from about 50 to about 125 mg of sapacitabine.

In one preferred embodiment, the medicament is administered in unit dosage form, said unit dosage containing from about 25 to about 600 mg of sapacitabine.

In a more preferred embodiment, the medicament is administered in unit dosage form, said unit dosage containing from about 25 to about 225 mg of sapacitabine.

More preferably, the medicament is administered in unit dosage form, said unit dosage containing from about 50 to about 125 mg of sapacitabine.

In one especially preferred embodiment, the medicament is administered twice daily in a unit dosage form containing about 20, 25, 60, 75, 100, 150, 150, 200, 300, 400 or 450 mg of sapacitabine.

In one preferred embodiment, the total daily dose is made up of one more unit dosages. Where more than one unit dosage is administered, the unit dosages may be the same or different.

In another especially preferred embodiment, the medicament is administered twice daily in a unit dosage form containing about 200 mg of sapacitabine.

In another especially preferred embodiment, the medicament is administered twice daily in a unit dosage form containing about 100 mg of sapacitabine.

In another especially preferred embodiment, the medicament is administered twice daily in a unit dosage form containing about 50 mg of sapacitabine.

In one preferred embodiment of the invention, the treatment cycle comprises:
(i) administering a therapeutically effective amount of sapacitabine on days 1 to n of a first week, wherein n is an integer from 2 to 6;
discontinuing said administration for (7−n) days;
administering a therapeutically effective amount of sapacitabine on days 1 to n of a second week, wherein n is an integer from 2 to 6;
discontinuing said administration for (7−n) days;
(ii) a one week rest period during which no sapacitabine is administered.

Contrary to prior art conventional dosing regimens for sapacitabine and related anticancer agents, the presently claimed dosing regimen involves administering the sapacitabine in short dosing periods (e.g. 2 to 6 days) each of which is followed by a sapacitabine-free period (for example, 1 to 5 days). These dosing/sapacitabine-free periods are then followed by a longer rest period (e.g. 1 week), before the cycle is preferably repeated two or more times.

Advantageously, breaking the dosing period of sapacitabine with a short rest period within each treatment cycle (i.e. two periods of 2 to 6 days, separated by a short rest period), allows the drug to be administered over a short time frame with maximum intensity and with as little toxicity as possible.

In one highly preferred embodiment, the sapacitabine is administered in a dosing regimen comprising at least one 21 day treatment cycle, wherein said treatment cycle comprises:
(i) administering a therapeutically effective amount of sapacitabine on days 1 to 3 of the treatment cycle;
discontinuing said administration for days 4 to 7 of the treatment cycle;
administering a therapeutically effective amount of sapacitabine on days 8 to 10 of the treatment cycle;
discontinuing said administration for days 11 to 14 of the treatment cycle;
(ii) a rest period for days 15 to 21 of the treatment cycle during which no sapacitabine is administered.

In another especially preferred embodiment, the sapacitabine is administered in a dosing regimen comprising at least one 21 day treatment cycle, wherein said treatment cycle comprises:
(i) administering a therapeutically effective amount of sapacitabine on days 1 to 5 of the treatment cycle;

discontinuing said administration for days 6 and 7 of the treatment cycle;
administering a therapeutically effective amount of sapacitabine on days 8 to 12 of the treatment cycle;
discontinuing said administration for days 13 and 14 of the treatment cycle;
(ii) a rest period for days 15 to 21 of the treatment cycle during which no sapacitabine is administered.

Another embodiment of the invention relates to the use of sapacitabine, or a metabolite thereof, in the preparation of a medicament for treating CTCL, wherein the sapacitabine is administered in a dosing regimen comprising at least one 21 day treatment cycle, wherein said treatment cycle comprises:
(i) administering a therapeutically effective amount of sapacitabine on days 1 to 3 of the treatment cycle;
discontinuing said administration for days 4 to 7 of the treatment cycle;
administering a therapeutically effective amount of sapacitabine on days 8 to 10 of the treatment cycle;
discontinuing said administration for days 11 to 14 of the treatment cycle;
(ii) a rest period for days 15 to 21 of the treatment cycle during which no sapacitabine is administered.

In one preferred embodiment, the sapacitabine is administered in 50-300 mg unit dosage form twice daily, more preferably, in 100-300 mg unit dosage form twice daily, even more preferably, in 250-300 mg unit dosage form twice daily.

In one highly preferred embodiment, the sapacitabine is administered in 100 mg or 200 mg unit dosage form twice daily, more preferably, 200 mg. Alternatively, the sapacitabine is administered in 50 mg unit dosage form twice daily.

Another embodiment of the invention relates to the use of sapacitabine, or a metabolite thereof, in the preparation of a medicament for treating CTCL, wherein the sapacitabine is administered in a dosing regimen comprising at least one 21 day treatment cycle, wherein said treatment cycle comprises:
(i) administering a therapeutically effective amount of sapacitabine on days 1 to 5 of the treatment cycle;
discontinuing said administration for days 6 and 7 of the treatment cycle;
administering a therapeutically effective amount of sapacitabine on days 8 to 12 of the treatment cycle;
discontinuing said administration for days 13 and 14 of the treatment cycle;
(ii) a rest period for days 15 to 21 of the treatment cycle during which no sapacitabine is administered.

Preferably, for this embodiment, the sapacitabine is administered in 50-200 mg unit dosage form twice daily, or 50-125 mg unit dosage form twice daily. More preferably, the sapacitabine is administered in 50 mg or 100 mg unit dosage form twice daily, even more preferably, 100 mg unit dosage form twice daily.

Another embodiment of the invention relates to the use of sapacitabine, or a metabolite thereof, in the preparation of a medicament for treating leukemia, wherein the sapacitabine is administered in a dosing regimen comprising at least one 21 day treatment cycle, wherein said treatment cycle comprises:
(i) administering a therapeutically effective amount of sapacitabine on days 1 to 3 of the treatment cycle;
discontinuing said administration for days 4 to 7 of the treatment cycle;
administering a therapeutically effective amount of sapacitabine on days 8 to 10 of the treatment cycle;
discontinuing said administration for days 11 to 14 of the treatment cycle;
(ii) a rest period for days 15 to 21 of the treatment cycle during which no sapacitabine is administered.

Preferably, for this embodiment, the medicament is administered in unit dosage form, said unit dosage containing about 375 mg to about 475 mg of sapacitabine.

In one particularly preferred embodiment, the medicament is administered in unit dosage form, said unit dosage increasing incrementally with each treatment cycle.

More preferably, the medicament is administered in unit dosage form, said unit dosage containing about 375 mg and increasing in 50 mg increments with each treatment cycle to a maximum of 1200 mg.

Advantageously, the above described dosing regimens maximise drug efficiency, whilst minimising adverse side effects associated with the treatment, such as immunosuppression, for example. Immunosuppression is a serious side effect suffered by many CTCL patients because most patients have immunologic impairment as a result of the underlying disease. In addition, because of the pre-existing immunocompromised condition of these patients, the additive immunosuppression that can result from drug treatment and the presence of skin lesions, patients are at increased for severe opportunistic infections. The present study suggests that administering sapacitabine to the patient over a short duration helps alleviate such adverse immunosuppressive side effects.

Yet another embodiment of the invention relates to the use of sapacitabine, or a metabolite thereof, in the preparation of a medicament for treating a proliferative disorder, wherein the sapacitabine or metabolite thereof is administered in a dosing regimen comprising at least one treatment cycle, wherein said treatment cycle comprises:
(i) administering a therapeutically effective amount of sapacitabine or metabolite thereof for about 2 to about 6 days per week, for 2 weeks;
(ii) a rest period of from about 5 to about 15 days during which no sapacitabine or metabolite thereof is administered or until treatment-related toxicities are resolved, whichever is longer.

Preferably, for this embodiment, the rest period is from about 7 to about 14 days, more preferably about 7 days.

A further aspect of the invention relates to a method of treating a proliferative disorder, said method comprising administering a therapeutically effective amount of sapacitabine, or a metabolite thereof, to a subject in accordance with a dosing regimen comprising at least one treatment cycle, wherein said treatment cycle comprises administering a therapeutically effective amount of sapacitabine or metabolite thereof for about 2 to about 6 days per week, for 2 weeks out of 3 weeks.

Yet another aspect of the invention relates to a method of treating a subject suffering from cutaneous T-cell lymphoma (CTCL), said method comprising administering a therapeutically effective amount of sapacitabine, or a metabolite thereof, to said subject.

A further aspect of the invention relates to a pharmaceutical composition for use in the treatment of cutaneous T-cell lymphoma (CTCL), said composition comprising sapacitabine, or a metabolite thereof, and a pharmaceutically acceptable carrier.

Preferably, said pharmaceutical composition further comprises a diluent and/or an excipient. Suitable pharmaceutically acceptable carriers, excipients and diluents are described below under the heading "Pharmaceutical Compositions".

Kit of Parts

Another aspect of the invention relates to a kit of parts comprising:

(i) a medicament comprising sapacitabine, or a metabolite thereof, admixed with a pharmaceutically acceptable diluent, excipient or carrier;
(ii) instructions to administer said medicament in accordance with a dosing regimen comprising at least one treatment cycle, wherein said treatment cycle comprises administering a therapeutically effective amount of sapacitabine or metabolite thereof for about 2 to about 6 days per week, for 2 weeks out of 3 weeks.

Preferred aspects of the dosing regimen set forth above apply equally to this embodiment of the invention.

Formulation

Preferably, the medicament used in the dosing regimen of the invention is for oral administration.

In one preferred embodiment, the medicament is in the form of a granulated powder fill capsule. Preferably, the medicament comprises (i) a capsule; and (ii) a core comprising sapacitabine and a solid excipient, diluent and/or carrier. Suitable pharmaceutically acceptable carriers, excipients and diluents are described below under the heading "Pharmaceutical Compositions".

Preferably, for this embodiment, the sapacitabine is in amorphous form.

Preferably, the capsule is a gelatin capsule.

More preferably, for this embodiment the core comprises a granulated mixture of sapacitabine, lactose, carmellose calcium, hydroxypropyl cellulose and calcium stearate.

In an alternative preferred embodiment, the medicament is in the form of a liquid fill formulation.

Preferably, the medicament comprises (i) a capsule; and (ii) a core comprising sapacitabine and a liquid carrier. Liquid fill formulations for sapacitabine are described in more detail in International Application PCT/GB2006/004927 (WO 2007/072061; Cyclacel Limited), the contents of which are herein incorporated by reference.

Advantageously, liquid fill formulations exhibit improved stability and can be stored at room temperature, compared to 4° C. for powder fill formulations. Furthermore, preliminary studies indicate that liquid fill formulations allow equivalent absorption of the active agent into the bloodstream and, in the case of human dosing, show similar pharmacodynamic effects. Finally, the process for preparing liquid fill formulations has manufacturing advantages in that it minimises the handling of the cytotoxic active agent in the powder form since once the mixing has taken place, all filling processes involve liquid handling without the need for extensive containment.

Preferably, for the liquid fill formulation, the sapacitabine is crystalline. More preferably, the sapacitabine is B-form crystalline sapacitabine.

Suitable capsule materials will be familiar to the person skilled in the art and include, for example, any polymeric material (polymers or copolymers, natural or synthetic) possessing the desired physical characteristics to allow delivery of the active agent by oral administration.

By way of example, suitable capsules include those prepared from water-soluble cellulose derivatives, a gelling agent and a co-gelling agent (see for example, U.S. Pat. No. 5,431,917). Other examples include capsules prepared from hydroxypropyl methylcellulose and an ammonium salt of cellulose acetate phthalate polymer, or capsules prepared from gelatin and an ammonium salt of a copolymer of methacrylic acid and methacrylic acid alkyl ester.

Further examples include polymers obtainable by the polymerization of at least one vinyl ester in the presence of one or more polyether-containing compounds and, where appropriate, one or more other copolymerizable monomers (see for example, U.S. Pat. No. 6,783,770).

Other suitable capsule materials include polymers or copolymers obtained by polymerizing or copolymerizing at least one polymerizable vinyl monomer in the presence of polyvinyl alcohol and/or derivatives thereof (see for example, US20050186268). Unlike conventional capsules, hard capsules of this type are compatible with liquid or semi-liquid cores.

Preferably, the capsule is a hard capsule, although soft capsules can also be used.

Preferably, for this embodiment, the capsule is a gelatin capsule. Gelatin capsules may be prepared using conventional techniques (see eg. The Theory and Practice of Industrial Pharmacy, Ed. Lachman L. et al, Third Edition, Lea & Febiger, 1986, Philadelphia, pp. 398-412).

Preferably, the capsule is sealed by a gelatin band.

In one preferred embodiment, the capsule comprises one or more opacifying agents and/or one or more pigments.

Preferably, the pigments and/or opacifying agents are each present in an amount of about 0.1 to about 10% by weight.

Suitable pigments include, for example, titanium dioxide, laked pigments (e.g. FS&C aluminium lakes or D&C lakes), iron oxide pigments, natural colorants, synthetic oxides or the like, or a dyestuff selected from indigo, carmine, quinoline yellow, orange yellow S, curcurmin, riboflavin and cochineal.

An especially preferred opacifying agent is titanium dioxide. More preferably, the titanium dioxide is present in an amount of about 2%.

In addition, the capsule material may also contain other additives. These include, but are not limited to, absorbents, acids, adjuvants, anticaking agent, glidants, antitacking agents, antifoamers, anticoagulants, antimicrobials, antioxidants, antiphlogistics, astringents, antiseptics, bases, binders, chelating agents, sequestrants, coagulants, coating agents, colorants, dyes, pigments, compatiblizers, complexing agents, softeners, crystal growth regulators, denaturants, dessicants, drying agents, dehydrating agents, diluents, dispersants, emollients, emulsifiers, encapsulants, enzymes, fillers, extenders, flavor masking agents, flavorants, fragrances, gelling agents, hardeners, stiffening agents, humectants, lubricants, moisturizers, bufferants, pH control agents, plasticizers, soothing agents, demulcents, retarding agents, spreading agents, stabilizers, suspending agents, sweeteners, disintegrants, thickening agents, consistency regulators, surfactants, opacifiers, polymers, preservatives, antigellants, rheology control agents, UV absorbers, tonicifiers and viscomodulators. One or more additives from any particular class, as well as one or more different classes of additives, may be present in the compositions. Specific examples of additives are well known in the art. Preferred additives include surfactants and polymers.

Preferably, substantially all the active agent is suspended in the liquid carrier. However, in some cases, the active agent may be partially solubilized and partially suspended in the liquid carrier.

In one particularly preferred embodiment, the active agent is suspended in the liquid carrier.

In another embodiment, the active agent is partially or fully dissolved in the liquid carrier.

In one particularly preferred embodiment, the liquid carrier is a medium chain triglyceride oil.

In one highly preferred embodiment, the medium chain triglyceride is fractionated coconut oil or caprilyic/capric triglyceride. Commercially available Myglyol 812N is particularly preferred.

At room temperature, Myglyol 812N (also known as MCT, DAC, oleum neutrale, CTFA, caprilyic/capric triglyceride (caprylic acid: $C_8$, capric acid: $C_{10}$)) is a liquid lipid oil of low viscosity. Usually, MCT fatty acid composition is dominated by C8 fatty acids (50 to 65%), followed by $C_{10}$ (30 to 45%), $C_{12}$ (max 5%) and $C_6$ (max 3%). The oil is known to be more biodegradable than lipids with longer fatty acid chains. Due to the absence of toxicity on skin and mucous membranes, MCT has applications in dermal products where it enhances permeation and spreading. MCT is also widely used in oral formulations as a lubricant and drug solvent, and as a solution enhancer in parenteral formulations.

In an alternative embodiment, the liquid carrier comprises polyglycolized glycerides, for example, Gelucire®.

Gelucire compositions are inert semi-solid waxy materials which are amphiphilic in character and are available with varying physical characteristics. They are surface active in nature and disperse or solubilize in aqueous media forming micelles, microscopic globules or vesicles. They are identified by their melting point/HLB value. The melting point is expressed in degrees Celsius and the HLB (Hydrophile-Lipophile Balance) is a numerical scale extending from 0 to approximately 20. Lower HLB values denote more lipophilic and hydrophobic substances, and higher values denote more hydrophilic and lipophobic substances. The affinity of a compound for water or for oily substances is determined and its HLB value is assigned experimentally. One or a mixture of different grades of Gelucire excipient may be chosen to achieve the desired characteristics of melting point and/or HLB value.

Preferred Gelucires for use in the present invention include Gelucire® 44/14, 53/10, 50/13, 42/12, and 35/10 from the Gaftefossé company.

Gelucire 50/13 compositions are polyglycolized glycerides that are prepared by the alcoholysis reaction of natural oils with polyethylene glycols (PEG). They are mixtures of monoesters, diesters and/or triesters of glycerides of long chain ($C_{12}$ to $C_{18}$) fatty acids, and PEG (mono- and/or di-) esters of long chain ($C_{12}$ to $C_{18}$) fatty acids and can include free PEG. Gelucire compositions are generally described herein as fatty acid esters of glycerol and PEG esters or as polyglycolized glycerides.

The large family of Gelucire compositions is characterized by a wide range of melting points of from about 33° C. to about 64° C. and most commonly from about 35° C. to about 55° C., and by a variety of HLB values of from about 1 to about 14, most commonly from about 7 to about 14. For example, Gelucire 50/13 designates a melting point of approximately 50° C. and an HLB value of about 13 to this grade of Gelucire. The appropriate choice of melting point/HLB value of a Gelucire or a mixture of Gelucire compositions will provide the delivery characteristics needed for a specific function, e.g., immediate release, sustained release, and the like. The low melting points of many of the solid Gelucire compositions provide a means of incorporating the pharmaceutically active ingredients in them at temperatures from about 0° C. to about 50° C. above their respective melting points, and then filling the melt (solution and/or dispersion) in hard gelatin capsules. The melt solidifies inside the capsules upon cooling to room temperature.

In one highly preferred embodiment of the invention, the liquid carrier comprises Gelucire 44/14. This carrier is a semi-solid excipient which is a mixture of glycerol and PEG1500 esters of long chain fatty acids. The suffixes 44 and 14 refer to its melting point and hydrophilic/lipophilic balance (HLB) respectively. Gelucire 44/14 is commercially available (CAS 121548-04-7) and is also known as PEG 32 glycerol laurate.

Gelucire 44/14 and Miglyol 812N can be used either alone, or in combination with one or more other co-carriers or additives. In one preferred embodiment, Miglyol 812N is used in combination with colloidal silicon dioxide (Aerosil 200). Preferably, the Miglyol 812N is used with up to 2% combination colloidal silicon dioxide.

Advantageously, formulations comprising Myglyol 812N and Gelucire 44/14 both show excellent stability superior to other formulations. Myglyol 812N is particularly preferred as the liquid carrier in view of its more favourable viscosity properties.

In one embodiment of the invention, the core may further comprise additional ingredients, for example, one or more vegetable oils, especially arachidis oil or sesame oil, or other pharmaceutically acceptable diluents, excipients or carriers. The core may also contain one or more solubilisers, one or more surfactants and/or one ore more co-surfactants. A preferred solubilizer is diethylene glycol monoethyl ether. Preferred surfactants include caprylocaproyl macrogolglycerides or polyoxyethylene castor oil derivatives. Particularly preferred polyoxyethylene castor oil derivatives are polyoxyl (40) hydrogenated castor oil or polyoxyl (35) hydrogenated castor oil. A preferred co-surfactant is polyethylene glycol 400. A preferred viscosity imparter is polyvinylpyrrolidone. A particularly preferred viscosity imparter is povidone (PVP K-30).

Other examples of additional ingredients include colloidal silicon dioxide (for example, Aerosil 200), Gelucire 44/11, PEG4005, Polyoxamers 188 and 124, Lipoid PPL, Captex 200 and Labrafil.

Preferably, the amount of liquid carrier is from 2 to 50 parts by weight relative to 1 part by weight of sapacitabine.

More preferably, the amount of liquid carrier is from 2 to 10 parts by weight relative to 1 part by weight of sapacitabine.

Even more preferably, the amount of liquid carrier is from 2 to 5 parts by weight relative to 1 part by weight of sapacitabine.

More preferably still, the amount of liquid carrier is about 3 parts by weight relative to about 1 part by weight of sapacitabine.

In one highly preferred embodiment, the core comprises 25% w/w of active agent and 75 w/w of liquid carrier.

In one highly preferred embodiment, the core consists essentially of crystalline sapacitabine and a liquid carrier.

In a more preferred embodiment, the core consists of sapacitabine and the liquid carrier alone, i.e. no other ingredients are present.

Active Agent

Sapacitabine was first disclosed in EP 536936 (Sankyo Company Limited; equivalent to JP 2569251) and was demonstrated to have excellent anti-tumour activity.

Subsequently, various crystal forms of sapacitabine have been disclosed (see for example EP 1364959; European application derived from WO 02/64609 in the name of Sankyo Company Limited). These crystal forms exhibit improved storage stability and ease of handling, whilst retaining a desirable pharmacokinetic profile.

In one particularly preferred embodiment of the invention, the active agent is crystalline and comprises the B-form of sapacitabine.

In one especially preferred embodiment, the active agent consists essentially of the B-form of sapacitabine.

In one especially preferred embodiment, the active agent consists of the B-form of sapacitabine. The B-form of sapacitabine can be prepared in accordance with the teachings of EP 1364959. Sapacitabine itself is prepared in accordance with the teachings of EP 536936.

By way of summary, 2'-cyano-2'-deoxy-1-β-D-arabinofuranosylcytosine monohydrochloride is passed through an ion-exchange resin (CHCOO⁻ type) to form 2'-cyano-2'-deoxy-1-β-D-arabinofuranosylcytosine. This compound is subsequently reacted with 1,3-dichloro-1,1,3,3-tetraisopropyldisiloxane to form 2'-cyano-2'-deoxy-3',5'-O-(1,1,3,3-tetraisopropyldisiloxane-1,3-diyl)-1-β-D-arabinofuranosylcytosine, which is in turn reacted with palmitic acid to form 2'-cyano-2'-deoxy-N$^4$-palmitoyl-3',5'-O-(1,1,3,3-tetraisopropyldisiloxane-1,3-diyl)-1-β-D-arabinofuranosylcytosine. The final step involves deprotection using tetrabutylammonium fluoride to form the desired product, 2'-cyano-2'-deoxy-N$^4$-palmitoyl-1-β-D-arabinofuranosylcytosine (sapacitabine).

Alternatively, sapacitabine can be prepared by reacting 2'-cyano-2'-deoxy-1-β-D-arabinofuranosylcytosine with palmitic anhydride.

The B form of sapacitabine is prepared by adding methyl acetate containing water at approximately 2.5 vol % to sapacitabine and heating to approximately 55° C. to prepare a clear solution. Subsequently, the solution is cooled under specific conditions and plate crystals are separated out of solution. After further stirring, the separated crystals are collected by filtration and washed with methyl acetate containing water at 2.5 vol % to afford the desired crystal B.

Proliferative Disorders

The dosing regimen of the invention is suitable for treating a variety of different proliferative disorders. Preferably, the subject in need of treatment is a mammal, more preferably a human.

In one preferred embodiment, the proliferative disorder is cancer or leukemia.

Preferably, the cancer is a solid tumour or lymphoma.

In one preferred embodiment, the cancer is lung cancer.

Lung cancers (bronchogenic carcinomas) may be divided into two broad categories namely, small cell lung cancer (SCLC) and non-small cell lung cancer (NSCLC). The distinction between these two types of cancer is based on the appearance of the tumour cells when viewed under a microscope.

SCLC accounts for 20% of lung cancers diagnosed and is characterised by small cells which are mostly filled with the nucleus (hence the name). It is sometimes also referred to as "oat cell" cancer. SCLC is the most aggressive type of cancer, which metastasizes rapidly to other parts of the body. Diagnosis with SCLC often occurs only after the cancer has spread throughout the body. In general, SCLC is almost always caused as a result of smoking.

NSCLC can be subdivided into a group of related lung cancers which include epidermoid or squamous cell carcinoma, adenocarcinoma and large cell carcinoma. Squamous cell lung cancer accounts for approximately 30% of all lung cancer cases and develops from reserve cells (which have the role of replacing damaged epithelium cells) in the lining of the lungs and bronchi. As a result, the cancer often initially develops in the centre of the chest. Squamous cell lung cancers are frequently slow growing and can take several years to progress from a confined tumour into invasive cancer. In 10-20% of cases, the cancer cavitates within the lungs. On metastasis, it often spreads to the bone, liver, adrenal glands, small intestine and brain.

Adenocarcinoma is the most common form of lung cancer making up 30-40% of all lung cancer cases. Adenocarcinoma develops in the outer part of the lung and develops from mucus-producing cells. The course of this cancer varies widely but often progresses slowly and the patient will present with few or no symptoms. In some cases, however, it can be extremely aggressive and rapidly fatal. In 50% of cases when it metastasises, it spreads only to the brain. Other locations to which adenocarcinoma spreads include the liver, the adrenal glands and bone.

The incidence of large cell carcinoma occurs less frequently than that of either adenocarcinoma or squamous cell carcinoma and accounts for 10-20% of lung cancer cases. The cancer is composed of large-sized cells that are anaplastic in nature and often arise in the bronchi. Large cell carcinoma develops on the periphery of the lungs and can spread to the plura.

Currently, lung cancer may be treated by surgery, radiation therapy or chemotherapy. Chemotherapy may be administered either alone or in combination with the other treatment options. Common NSCLC drugs and regimens include Camptosar® (irinotecan; CPT-11), camptothecin, Paraplatin® (carboplatin), Platinol® (cisplatin), epirubicin, Gemzar® (gemcitabine), Navelbine® (vinorelbine), oxaliplatin, Taxol® (paclitaxel) and Taxotere® (docetaxol) (NSCLC Treatment—Chemotherapy, Lung Cancer Online). However, chemotherapy is not curative. Other disadvantages of this treatment include toxicity, bystander damage to normal tissues and drug resistance (W. Wang et al, Cancer Sci., 2005, 96(10), 706). Furthermore, studies have shown that there is little survival benefit with some of the known treatments, such as vinorelbine (M. A. Socinski et al, Clin. Adv. Hematol. Oncol., 2003, 1(1), 33). Even a novel active such a troxacitabine has been shown to have little activity in NSCLC in 10 mg/m$^2$ doses administered intravenously over 30 minutes every three weeks (S. F. Dent et al, Lung, 2005, 183(4), 265).

In one particularly preferred embodiment of the invention, the cancer is non small cell lung cancer (NSCLC).

In another preferred embodiment, the proliferative disorder is a haematological malignancy, for example, advanced leukemias or myelodysplastic syndromes (MDS). Other examples include acute myelogenous leukemia (AML), acute lymphocytic leukemia (ALL) or chronic lymphocytic leukemia (CLL).

Advantageously, for AML patients with leukemia cutis, the presently claimed dosing regimens lead to significant shrinkage of leukemic infiltrates in the skin.

In one highly preferred embodiment, the proliferative disorder is AML. Preferably, the AML is previously untreated or first relapsed acute myeloid leukemia.

Even more preferably, the medicament is for treating AML in subjects of 60 years of age or more.

More preferably still, the medicament is for treating AML in subjects of 65 years of age or more.

More preferably still, the medicament is for treating AML in subjects of 70 years of age or more.

Preferably, for treating AML the sapacitabine is administered in a total daily dosage of from 375 mg to 475 mg, more preferably from 400 mg to 450 mg, even more preferably 410 to 440 mg, more preferably still 420 to 430 mg, even more preferably 425 mg. Preferably, the sapacitabine is administered twice daily.

Preferably, for treating AML the treatment cycle comprises administering a therapeutically effective amount of sapacitabine for 3 consecutive days per week, for 2 weeks, followed by a 7 day rest period.

Another aspect of the invention relates to the use of sapacitabine, or a metabolite thereof, in the preparation of a medicament for treating AML in elderly subjects, wherein the sapacitabine or metabolite thereof is administered in a dosing regimen comprising at least one treatment cycle, wherein said treatment cycle comprises:
(i) administering a therapeutically effective amount of sapacitabine or metabolite thereof for about 2 to about 6 days per week, for 2 weeks;
(ii) a rest period of from about 5 to about 15 days during which no sapacitabine or metabolite thereof is administered.

As used herein, the term "elderly subject" refers to patients of 60 years of age or over. More preferably, the subjects are 65 years of age or over, more preferably 70 years of age or over.

Preferably, the treatment cycle comprises administering a therapeutically effective amount of sapacitabine for 3 consecutive days per week, for 2 weeks, followed by a 7 day rest period.

Even more preferably, the sapacitabine is administered twice daily at a dosage of about 400 mg to about 425 mg for 3 consecutive days a week, for 2 weeks, every 21 days. More preferably, the sapacitabine is administered twice daily at a dosage of about 425 mg for 3 consecutive days a week, for 2 weeks, every 21 days.

Cutaneous T-Cell Lymphoma (CTCL)

In one highly preferred embodiment of the invention, the proliferative disorder is cutaneous T-cell lymphoma (CTCL).

Advantageously, treatment of CTCL with sapacitabine maximises drug efficiency, whilst minimising adverse side effects such as immunosuppression. Immunosuppression is a serious side effect suffered by many CTCL patients because most patients have immunologic impairment as a result of the underlying disease. In addition, because of the pre-existing immunocompromised condition of these patients, the additive immunosuppression that can result from drug treatment and the presence of skin lesions, patients are at increased for severe opportunistic infections. The present study suggests that administering sapacitabine to the patient helps alleviate such adverse immunosuppressive side effects.

Cutaneous T-cell lymphomas (CTCL) are a group of lymphoproliferative disorders characterized by localization of the neoplastic T-cell lymphocytes to the skin at presentation. Mycosis fungoides (MF) and Sezary syndrome (SS) make up the majority of these diseases (Siegel R S et al, Primary cutaneous T-cell lymphoma: review and current concept. Clin Oncol 18: 2908-2925, 2000).

MF and SS are low-grade lymphomas with skin manifestations, ranging from scaly patches or plaques in early stage to generalized erythroderma and tumours in advanced stage. In addition to being disfiguring, tumours may ulcerate, causing recurrent infection and chronic pain. Some patients also experience unremitting pruritus, fever, and chills (Duvic M et al, Quality-of-life improvements in cutaneous T-cell lymphoma patients treated with denileukin diftitox (ONTAK), Clin Lymphoma 2(4): 222-228, 2002). Cure is generally not attainable and the goals of treatment are symptom relief and improvement of skin conditions (Siegel R S et al, Primary cutaneous T-cell lymphoma: review and current concept, Clin Oncol 18: 2908-2925, 2000).

There are multiple therapeutic options for MF and SS. The FDA approved systemic therapies include Targretin® (bexarotene), Zolinza™ (vorinostat), Ontak® (denileukin diftitox) and photophoresis. Despite the effectiveness of these treatments, responses are usually not durable and there are significant treatment-related toxicities. New effective drugs and dosing regimens are needed to improve the treatment of these diseases.

Nucleoside analogues are a major group of antitumour cytotoxic drugs which appear to have activity in CTCL. Gemcitabine, an analogue of deoxycytidine, was reported to have a response rate of 60-70% in CTCL (Zinzani P L et al, Gemcitabine treatment in pretreated CTCL lymphoma: Experience in 44 patients; J of Clin Oncol 18: 2603-2606, 2000; Sallah S et al, Treatment of relapsing T-cell malignancies using gemcitabine; British J of Hematology 118: 185-187, 2001; Duvic M et al, Phase II evaluation of gemcitabine monotherapy for cutaneous T-cell lymphoma; Clin Lymphoma Myeloma 7 (1): 5 1-58, 2006). Sapacitabine is a rationally designed analogue of deoxycytidine with a unique mechanism of action and good oral bioavailability. In preclinical studies, it demonstrated significant activity against a wide range of malignancies. The major toxicity of sapacitabine is myelosuppression which appears to be determined by total daily dose and the length of consecutive days of dosing, which is similar to gemcitabine, where the MTD was found to be dependent on the dose and frequency of infusion (Duvic M et al, Phase II evaluation of gemcitabine, monotherapy for cutaneous T-cell lymphoma. Clin Lymphoma Myeloma 7 (1): 5 1-58, 2006; Kaye S B, Current status of phase I and II trials. J of Clin Oncol 12: 1527-153 1, 1994).

In one preferred embodiment, the cutaneous T-cell lymphoma is advanced untreated cutaneous T-cell lymphoma.

In one preferred embodiment, the cutaneous T-cell lymphoma is pretreated cutaneous T-cell lymphoma.

In one highly preferred embodiment, the cutaneous T-cell lymphoma is Mycosis fungoides (MF).

In one highly preferred embodiment, the cutaneous T-cell lymphoma is Sezary syndrome (SS).

Another aspect of the present invention relates to the use of sapacitabine, or a metabolite thereof, or a pharmaceutically acceptable salt thereof, in the preparation of a medicament for treating cutaneous T-cell lymphoma.

Preferably, the sapacitabine, or metabolite thereof, is administered in combination with a pharmaceutically acceptable carrier, diluent or excipient. Suitable carriers, diluents and excipients are detailed below under the heading "Pharmaceutical Compositions".

Preferably, the sapacitabine or metabolite thereof is administered in accordance with the dosing regimen of the first aspect of the invention.

Pharmaceutical Compositions

Although sapacitabine can be administered alone, for human therapy it will generally be administered in admixture with a pharmaceutical carrier, excipient or diluent.

A preferred embodiment of the invention therefore relates to the administration of sapacitabine, or a metabolite thereof, in combination with a pharmaceutically acceptable excipient, diluent or carrier.

Examples of such suitable excipients for the various different forms of pharmaceutical compositions described herein may be found in the "Handbook of Pharmaceutical Excipients, $2^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985). Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Salts/Esters

The active agent of the present invention can be present in the form of a salt or an ester, in particular a pharmaceutically acceptable salt or ester.

Pharmaceutically acceptable salts of the active agent of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid.

Esters are formed either using organic acids or alcohols/hydroxides, depending on the functional group being esterified. Organic acids include carboxylic acids, such as alkanecarboxylic acids of 1 to 12 carbon atom's which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

The invention also includes where appropriate all enantiomers and tautomers of the active agent. The man skilled in the art will recognise compounds that possess optical properties (one or more chiral carbon atoms) or tautomeric characteristics. The corresponding enantiomers and/or tautomers may be isolated/prepared by methods known in the art.

Stereo and Geometric Isomers

The active agent of the invention may exist in the form of different stereoisomers and/or geometric isomers, e.g. it may possess one or more asymmetric and/or geometric centres and so may exist in two or more stereoisomeric and/or geometric forms. The present invention contemplates the use of all the individual stereoisomers and geometric isomers of the agent, and mixtures thereof. The terms used in the claims encompass these forms, provided said forms retain the appropriate functional activity (though not necessarily to the same degree).

The present invention also includes all suitable isotopic variations of the active agent or pharmaceutically acceptable salts thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^{2}H$, $^{3}H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^{3}H$ or $^{14}C$ is incorporated, are useful in drug and/or substrate tissue distribution studies. Tritiated, i.e., $^{3}H$, and carbon-14, i.e., $^{14}C$, isotopes are particularly preferred for their ease of preparation and detectability. Further, substitution with isotopes such as deuterium, i.e., $^{2}H$, may afford certain therapeutic advantages resulting from greater metabolic stability, for example, increased in vivo half-life or reduced dosage requirements and hence may be preferred in some circumstances. Isotopic variations of the agents of the present invention and pharmaceutically acceptable salts thereof can generally be prepared by conventional procedures using appropriate isotopic variations of suitable reagents.

Solvates

The present invention also includes solvate forms of the active agent of the present invention. The terms used in the claims encompass these forms.

Polymorphs

The invention furthermore relates to various crystalline forms, polymorphic forms and (an)hydrous forms of the active agent. It is well established within the pharmaceutical industry that chemical compounds may be isolated in any of such forms by slightly varying the method of purification and or isolation form the solvents used in the synthetic preparation of such compounds.

Prodrugs

The invention further includes the active agent of the present invention in prodrug form. Such prodrugs are generally compounds wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include esters (for example, any of those described above), wherein the reversion may be carried out be an esterase etc. Other such systems will be well known to those skilled in the art.

Administration

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

For oral administration, particular use is made of compressed tablets, pills, tablets, gellules, drops, and capsules.

Preferably, these compositions contain from 1 to 2000 mg and more preferably from 50-1000 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredients can be incorporated into a cream consisting of an aqueous emulsion of polyethylene glycols or liquid paraffin. The active ingredients can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-500 mg, of active ingredient per dose.

Compositions may be formulated in unit dosage form, i.e., in the form of discrete portions containing a unit dose, or a multiple or sub-unit of a unit dose.

In a particularly preferred embodiment, the combination or pharmaceutical composition of the invention is administered intravenously.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the active agent, the metabolic stability and length of action of the agent, the age, body weight, general health, sex, diet, mode and time of administration, rate of excretion, drug combination, the severity of the particular condition, and the individual undergoing therapy. Dosages and frequency of application are typically adapted to the general medical condition of the patient and to the severity of the adverse effects caused, in particular to those caused to the hematopoietic, hepatic and to the renal system. The dosages disclosed herein are exemplary of the average case. There can of course be individual instances where higher or lower dosage ranges are merited, and such are within the scope of this invention.

As described above, sapacitabine is preferably administered in a therapeutically effective amount, preferably in the form of a pharmaceutically acceptable amount. This amount will be familiar to those skilled in the art.

Combinations

In one preferred embodiment of the invention, the sapacitabine or metabolite thereof is administered in combination with one or more other antiproliferative agents. In such cases, the compounds of the invention may be administered consecutively, simultaneously or sequentially with the one or more other antiproliferative agents.

It is known in the art that many drugs are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining drugs are that it may promote additive or possible synergistic effects through biochemical interactions and also may decrease the emergence of drug resistance which would have been otherwise responsive to initial treatment with a single agent.

Beneficial combinations may be suggested by studying the activity of the test compounds with agents known or suspected of being valuable in the treatment of a particular disorder. This procedure can also be used to determine the order of administration of the agents, i.e. before, simultaneously, or after delivery.

The present invention is further illustrated by way of the following non-limiting examples.

EXAMPLES

Example 1

The B-form of sapacitabine was prepared in accordance with the methodology described in EP 536936 and EP 1364959, both in the name of Sankyo Company Limited.

Capsule Preparation

Liquid fill capsules were prepared in accordance with the methodology described in PCT/GB2006/004927 (WO 2007/072061; Cyclacel Limited).

The drug is supplied as 25 mg and 75 mg opaque white, gelatin capsules. This formulation comprises liquid-filled capsules of a sapacitabine-B crystalline form in miglyol 812N. Capsules are packaged in high-density polyethylene bottles (50 capsules per bottle), with low-density polyethylene screw-cap, child-resistant closures. The higher strength was formulated to fill into a size 1 capsule, while the lower strength was formulated to fill into a size 3 capsule as appropriate. All materials are of pharmacopoeial quality. A summary of the formulation components is provided in the table below.

| | Formulation Capsule (mg/capsule) | |
|---|---|---|
| | Unit Formula | |
| Ingredient | 25 mg | 75 mg |
| Sapacitabine B Form | 25 mg | 75 mg |
| Miglyol 812N Ph. Eur/GRAS | 100 mg | 300 mg |
| Gelatin Capsule and gelatin banding USP/Ph. Eur. | Size 3 | Size 1 |

Ph. Eur = European Pharmacopoeia; GRAS: Generally regarded as safe; USP = United States Pharmacopoeia Preparation: Gelatin capsules are filled with above components under Good Manufacturing Practice (GMP) conditions.

Storage and Stability: The capsules should be stored at room temperature (15-25° C.) in a closed container, protected from light in a secure, limited-access storage area. Both capsule strengths (25 and 75 mg) are stable for at least 24 months.

The core formulation is a simple suspension prepared by mixing the active agent with Miglyol 812N. Myglyol 812N is also known as fractionated coconut oil and is described in the Ph. Eur and is GRAS listed. These are the only ingredients in the formulation apart from the capsule shell and banding material.

White capsule shells were used containing titanium dioxide USP/Ph. Eur. 2% (by weight) and Gelatin USP/Ph. Eur to 100%. The capsules were banded at the join of the body and cap to prevent leakage. The band material contains Gelatin USP/Ph. Eur.

Both strengths of capsule are manufactured from the same mix with the doses being differentiated by differences in fill weight. The capsules are prepared as follows:

1. Weigh the sapacitabine into the mixing vessel.
2. Add the Miglyol 812N incrementally until the correct total amount has been added.
3. Mix the two components using a Silverson mixer at high speed for 5-8 minutes.
4. Remove sample and check for homogeneity.
5. If homogeneous, draw a vacuum to degas the mixture.
6. Set up the Bosch 1500L capsule filler with size 3 change parts and adjusts the filling pump to give the desired fill weight for the 25 mg dose.
7. Fill the 25 mg capsules using the following targets for average of 12 capsules i.e. Warning 2.5%; Action 3.5%; Reject 5.0%. The limits on the individual capsules are 7.5%.
8. Repeat for the 75 mg capsules by replacing the size 3 change parts with size 1 change parts and resetting the fill weights. All other conditions are the same.
9. On completion of all capsule filling the capsules are banded using clear gelatin.

The fill weights for the two strengths of capsules are 100 mg and 300 mg, respectively.

The capsule shells and the gelatin for banding were obtained from the following suppliers: Capsule—Capsulgel Bornem, Rijksweg 11, B-2880 Bornem, Belgium); Gelatin (for capsule banding)—Stoess AG, Gammelsbacherstr. 2, 8412 Eberbach, Germany.

Treatment of CTCL

The study population for this trial is patients with advanced CTCL (stage IB or higher) who have had progressive, recurrent, or persistent disease on or following two systemic therapies.

Study Design and Plan

The study is an open label, randomized, phase II study. Eligible patients are randomized 1:1 to receive a high-dose or low-dose regimen using the above liquid fill capsule formulation:

High-dose (Arm A): 100 mg b.i.d.×3 consecutive days per week for 2 weeks followed by 1-week rest; subsequently modified to 200 mg b.i.d.×3 consecutive days per week for 2 weeks followed by 1-week rest Low-dose (Arm B): 50 mg b.i.d.×3 consecutive days per week for 2 weeks followed by 1-week rest; subsequently modified to 100 mg b.i.d.×3 consecutive days per week for 2 weeks followed by 1-week rest.

The randomized design ensures that the two dosing regimens are evaluated in a similar patient population. One treatment cycle is 3 weeks. Patients who receive the low-dose regimen may be crossed over to the high-dose regimen if they tolerate the low-dose regimen well but did not achieve at least a partial response after three cycles of treatment.

Treatment continues until: progressive disease; lack of efficacy; unacceptable toxicity; patient withdrawal of consent; investigator's discretion that it is in the best interest of the patient to withdraw; intercurrent illness or changes in patient's condition that renders patient ineligible, or continuing treatment of sapacitabine unsafe, or regular follow-up impossible; non-compliance with study medication or protocol-required evaluations and follow-up; or termination of the clinical trial by the sponsor.

Patients are monitored regularly with physical exams including skin assessment, lymph node assessment, photographs, laboratory tests, and appropriate tumour imaging studies. A post-treatment follow-up visit will be conducted within 4 weeks of administration of the last dose of the study drug, or prior to the initiation of new cancer treatment.

The primary efficacy endpoint is the response rate of overall skin disease as measured by a modified severity-weighted assessment tool (SWAT) by investigators in the clinic, with documentation by digital photographs.

Treatment of AML in Elderly Patients

The study population for this trial is elderly patients with acute myeloid leukemia (AML) previously untreated or in first relapse. The study is a randomized phase II study.

Eligible patients are those ≧70 years of age with histologically or pathologically confirmed AML who have not received any systemic therapy for AML or who are in first relapse after achieving CR to initial induction, consolidation and/or maintenance therapy. Patients receive 400 mg sapacitabine b.i.d.×3 consecutive days per week for 2 weeks followed by 7 day rest.

Treatment continues until: clinically significant progressive disease; lack of efficacy, unacceptable toxicity; patient withdrawal of consent; investigator's discretion that it is in the best interest of the patient to withdraw, intercurrent illness or changes in patient's condition that renders patient ineligible or continuing treatment of sapacitabine unsafe, or regular follow-up impossible; non-compliance with study medication or protocol-required evaluations and follow-up; or termination of the clinical trial by the sponsor.

Patients are monitored by physical examinations, laboratory tests, and appropriate tumour imaging studies. A post treatment follow-up visit will be conducted within 4 weeks after the last dose of the study drug, or prior to the initiation of new cancer treatment.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

The invention claimed is:

1. A method of treating a proliferative disorder which is selected from myelodysplastic syndrome (MDS) or acute myeloid leukemia (AML), said method comprising administering a therapeutically effective amount of sapacitabine, or a metabolite thereof, to a subject in need thereof in accordance with a dosing regimen comprising at least one treatment cycle, wherein said metabolite is 2'-C-Cyano-2'-deoxy-β-D-arabino-pentafuranosylcytosine (CNDAC) and said treatment cycle comprises:
   (i) administering a therapeutically effective amount of sapacitabine or metabolite thereof for 3 consecutive days per week, for 2 weeks followed by;
   (ii) a rest period of from about 5 to about 15 days during which no sapacitabine or metabolite thereof is administered or until treatment-related toxicities are resolved, whichever is longer.

2. A method according to claim 1 wherein the sapacitabine, or metabolite thereof, is administered twice daily.

3. A method according to claim 1 wherein the dosing regimen comprises at least two treatment cycles.

4. A method according to claim 1 wherein the cycles are repeated sequentially with a time lag between sequential cycles.

5. A method according to claim 1 wherein the sapacitabine, or metabolite thereof, is administered twice daily in a unit dosage form containing about 25, 75, 100, 150, 200, 300, 400 or 450 mg.

6. A method according to claim 1 wherein the sapacitabine, or metabolite thereof, is administered in a total daily dosage of from about 25 to about 600 mg.

7. A method according to claim 1 wherein the proliferative disorder is myelodysplastic syndrome (MDS).

8. A method according to claim 1 wherein the proliferative disorder is acute myeloid leukemia (AML).

9. A method according to claim 2 wherein the sapacitabine, or metabolite thereof, is administered twice daily in approximately equal dosages.

10. A method according to claim 6 wherein the sapacitabine, or metabolite thereof, is administered in a total daily dosage of about 25 mg to about 225 mg.

11. A method according to claim 6 wherein the sapacitabine, or metabolite thereof, is administered in a total daily dosage of about 50 mg to about 125 mg.

12. A method according to claim 1 wherein the sapacitabine, or metabolite thereof, is administered in a total daily dosage of about 375 mg to about 475 mg.

13. A method according to claim 1 wherein the sapacitabine, or metabolite thereof, is administered twice daily in a 50 to 300 mg unit dosage form.

14. A method according to claim 1 wherein the sapacitabine, or metabolite thereof, is administered twice daily in a 100 to 300 mg unit dosage form.

15. A method according to claim 1 wherein the sapacitabine, or metabolite thereof, is administered twice daily in a 50 to 200 mg unit dosage form.

16. A method according to claim 1 wherein the sapacitabine, or metabolite thereof, is administered twice daily at a dosage of about 400 to about 425 mg.

17. A method according to claim 1 wherein the sapacitabine, or metabolite thereof, is administered for 3 consecutive days a week for 2 weeks every 21 days.

* * * * *

UNITED STATES PATENT AND TRADEMARK OFFICE
CERTIFICATE OF CORRECTION

PATENT NO. : 8,536,188 B2
APPLICATION NO. : 12/597293
DATED : September 17, 2013
INVENTOR(S) : Chiao Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 408 days.

Signed and Sealed this
Third Day of November, 2015

Michelle K. Lee
*Director of the United States Patent and Trademark Office*